United States Patent [19]

Arndt et al.

[11] 4,380,396
[45] Apr. 19, 1983

[54] METHOD AND APPARATUS FOR MEASURING THE OPACITY OF SHEET MATERIAL

[75] Inventors: William A. Arndt; Wayne A. Damrau; Donald J. Gunderson, all of Wisconsin Rapids, Wis.

[73] Assignee: Consolidated Papers, Inc., Wisconsin Rapids, Wis.

[21] Appl. No.: 220,432

[22] Filed: Dec. 29, 1980

[51] Int. Cl.³ .......................................... G01N 21/01
[52] U.S. Cl. .................................................. 356/432
[58] Field of Search ................ 356/432, 434, 443, 444

[56] References Cited

U.S. PATENT DOCUMENTS 2,206,214 7/1940 Wicker ................................ 356/432
4,224,513 9/1980 Casey et al. ........................ 356/432
4,229,107 10/1981 Childers ............................. 356/443

OTHER PUBLICATIONS

Hüfner, "Semi-Automatic Interpretation of Spectral Plates Using the MD100 Microdensitometer and the KSR 4100 Minicomputer", Jena. Rev., (Germany), vol. 22, 1977, pp. 220-223.
Bothe, K., et al., "Microprocessor-Controlled Photometric Evaluation of High Speed Cinematographic Films", J. Physics, Sci. Instrom., vol. 12, (1979), pp. 201-204.
Revesz et al., "A Laser Scanner for the Densitometric Analysis of Radiographs", Med. Phys. 6(3), May/Jun., 1979, pp. 216-218.

*Primary Examiner*—Bruce Y. Arnold
*Attorney, Agent, or Firm*—Gary, Juettner & Pyle

[57] ABSTRACT

To measure the opacity of sheet material, such as paper, a beam of light is directed against the material and the intensity of any light passing through the material is sensed and converted to a visual readout. A plurality of opacity measurements are made at different areas on the sheet material and, when a selected number of measurements have been made, a readout of the average value of the measurements is generated. The particular technique enables a large number of opacity measurements to be quickly and conveniently made and averaged, and is considerably less complicated and time consuming than opacity measurements which are conventionally made as a function of contrast ratios.

4 Claims, 5 Drawing Figures

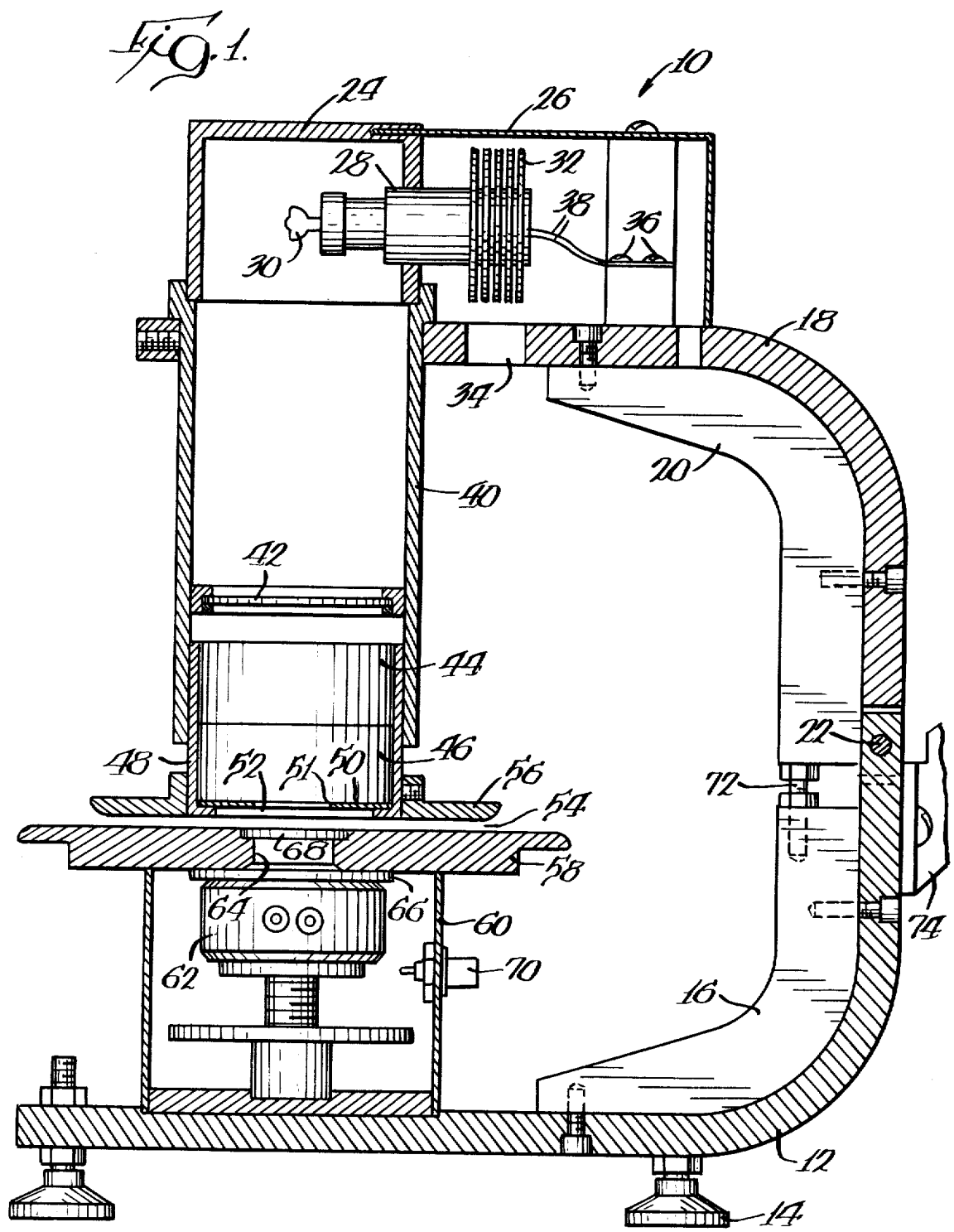

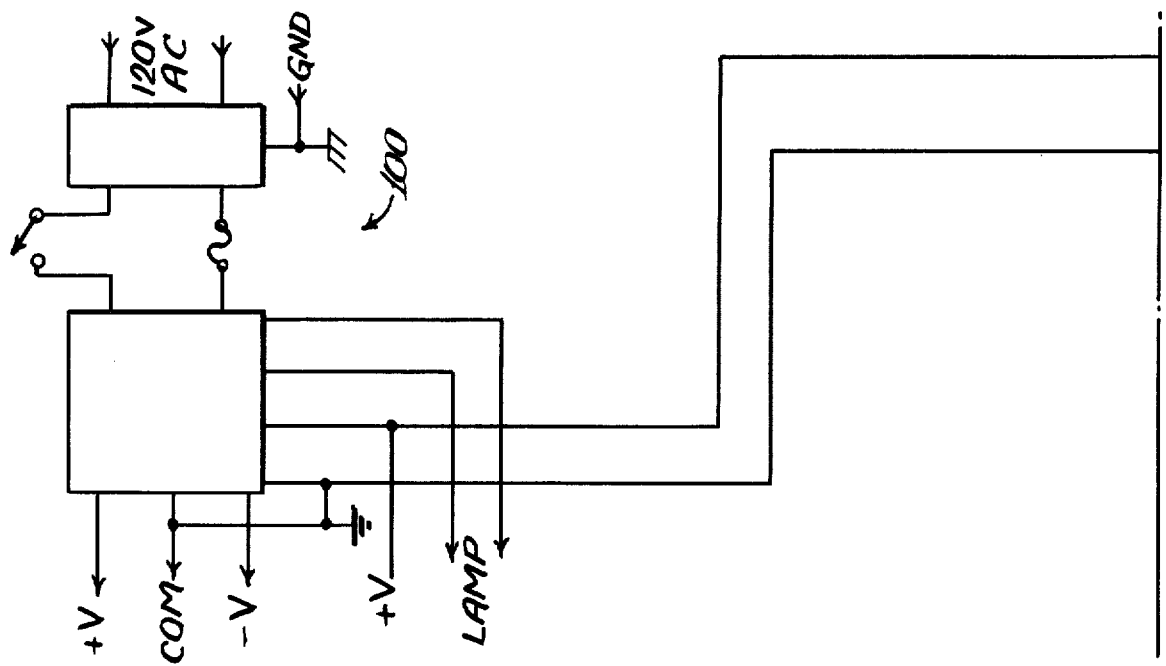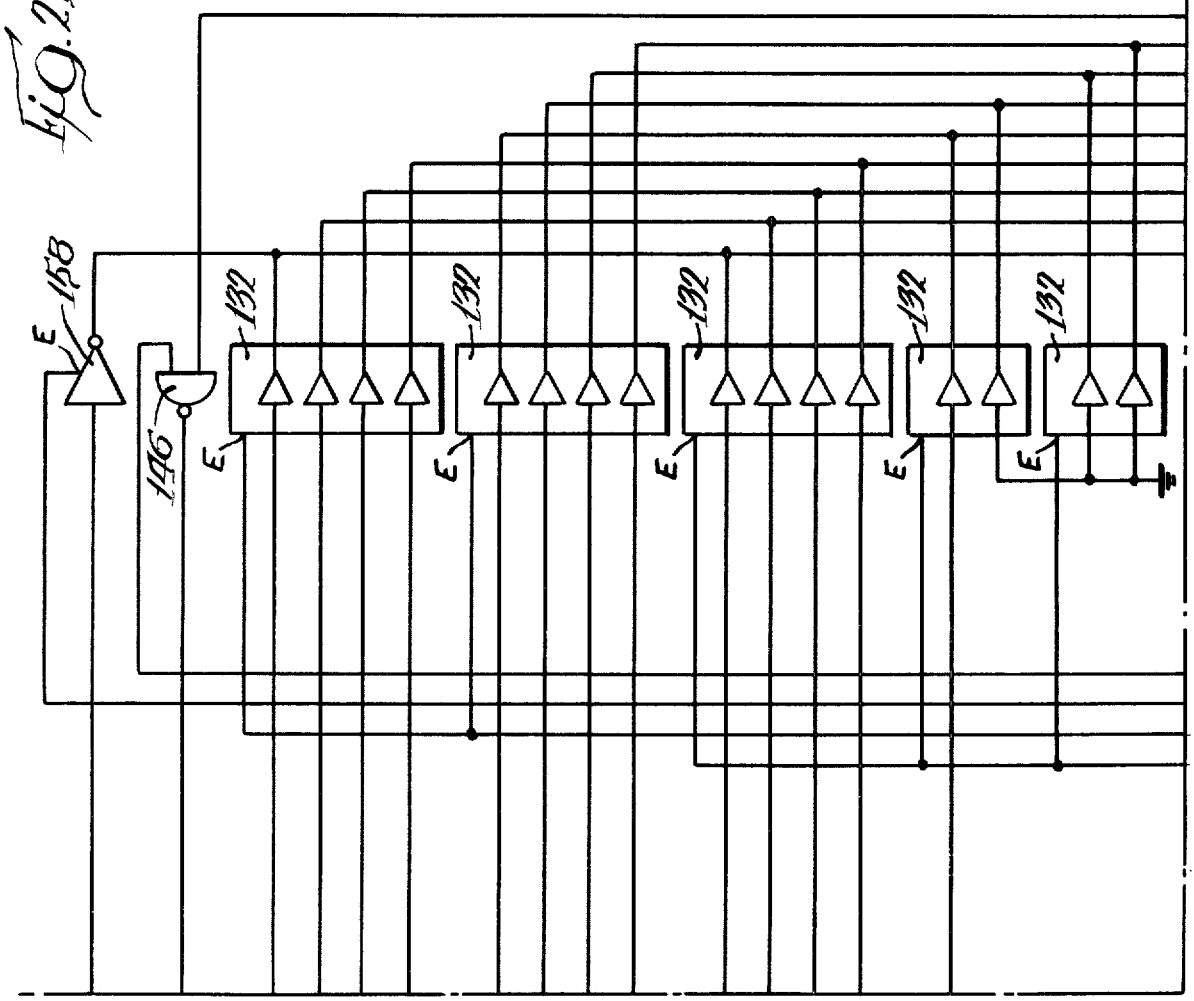
Fig. 2B.

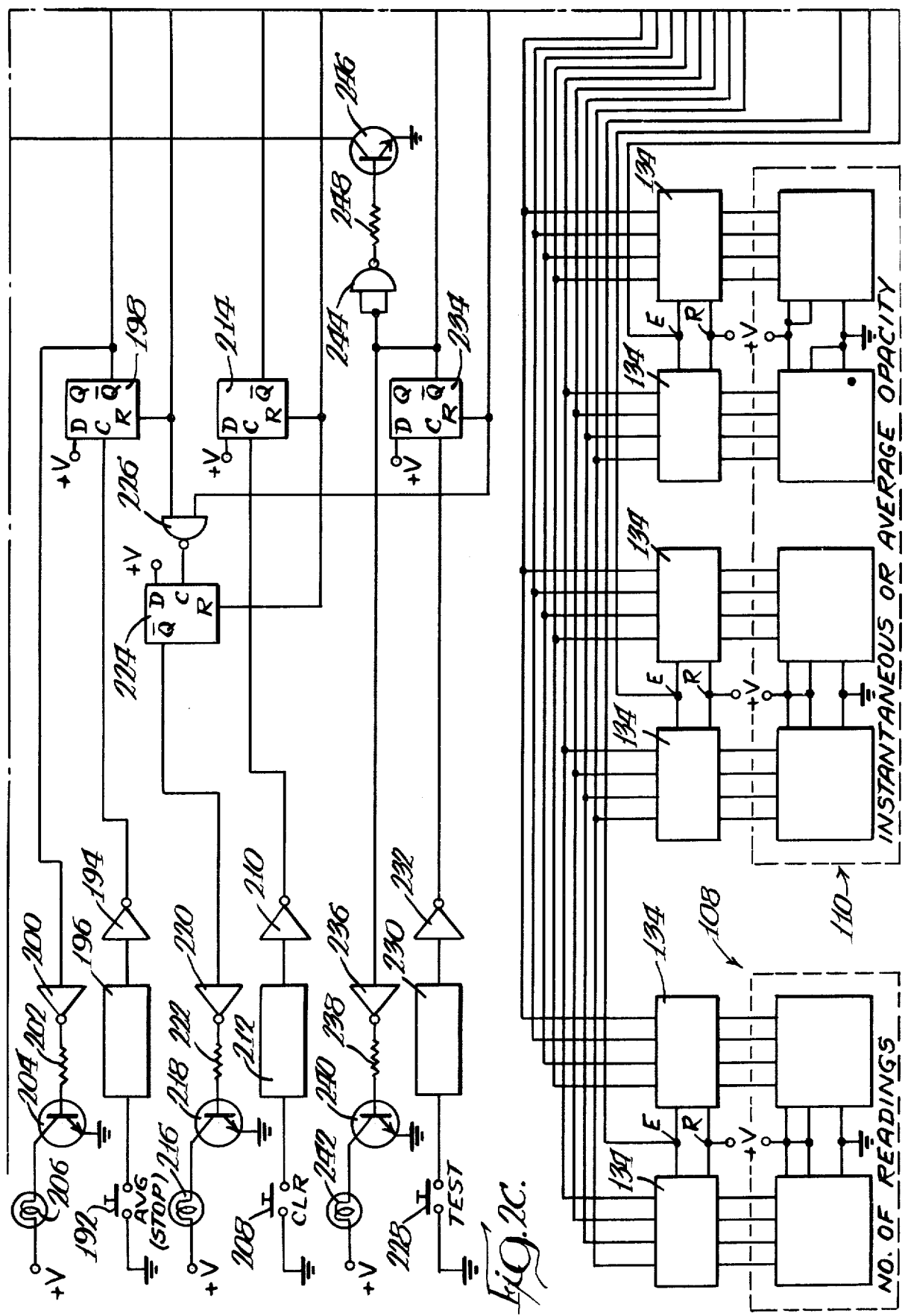

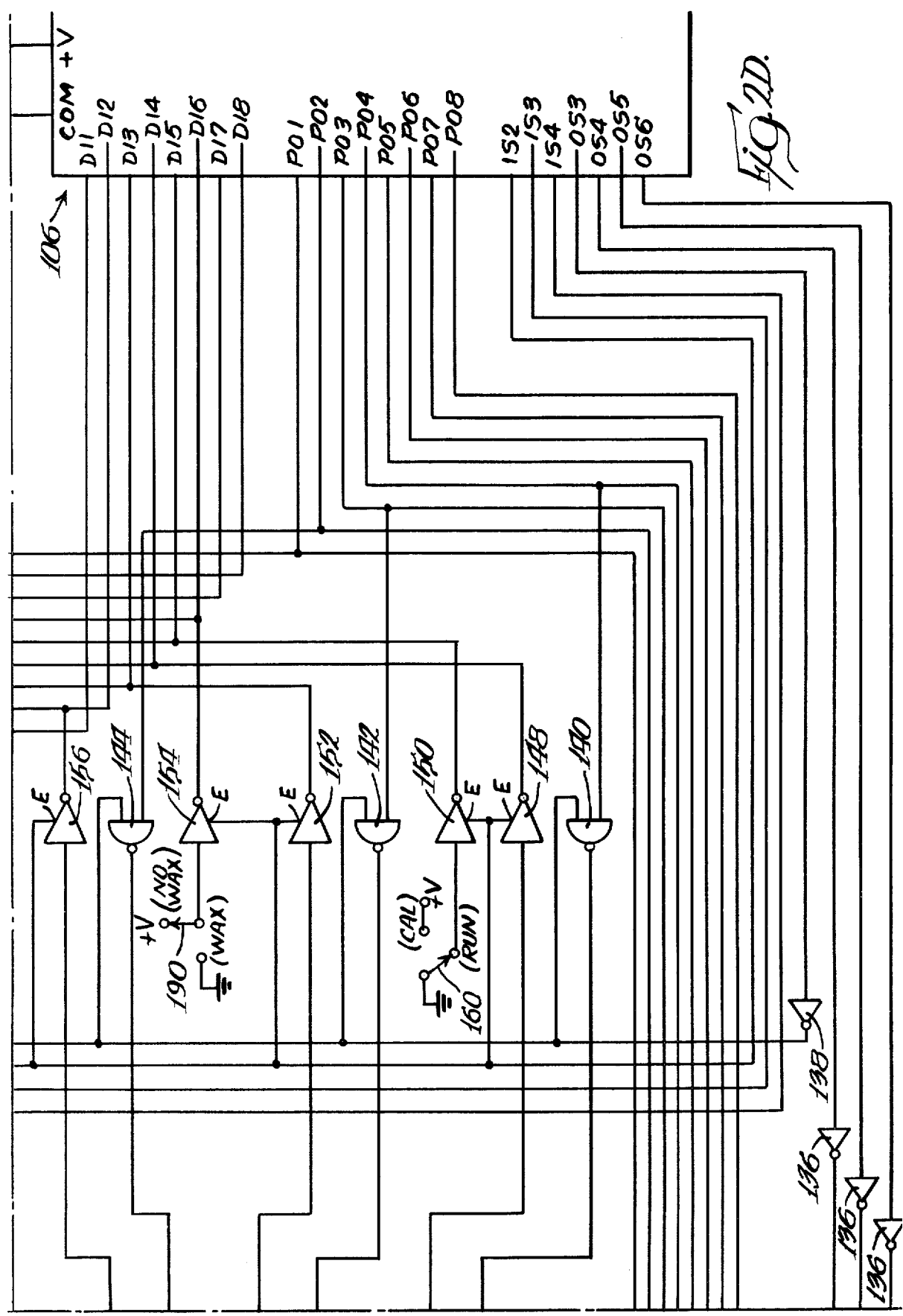

METHOD AND APPARATUS FOR MEASURING THE OPACITY OF SHEET MATERIAL

BACKGROUND OF THE INVENTION

The present invention relates to a method of and apparatus for measuring the opacity of sheet material, and in particular to a method and apparatus wherein the opacity of sheet material is determined as a function of the light transmission characteristics of the material.

In the manufacture of lightweight specialty packaging papers of the dry opaque and saturated waxed grades, such as may be used for cereal box overwraps, gum wrappers, paper/poly/foil/poly pouches, antiwater wicking labels, orange juice spiral canisters, potato chip bags, gift wrappings, etc., an important area of quality control resides in the ability to manufacture such packaging papers to have specified opaque grade structures. The required degree of opacity in such papers is developed through the use of titanium dioxide and controlled through a series of rigid manufacturing specifications.

As a result of customer demands on the paper industry, grade specifications of papers and the quantity and cost of titanium dioxide, there exists a need to accurately measure opacity of paper products of both the dry opaque and saturated waxed grades. As is known, opacity is a fundamental optical property of paper as a whole, yet measurement of opacity is empirical. The opacity of a sheet of paper is influenced by the amounts and kinds of fillers, the degree of bleaching of the fibers, types of coating materials applied to the papers and, when used, the thickness of the wax. Throughout the paper industry as a whole, opacity has heretofore been evaluated as a function of contrast ratio measurements, generally following TAPPI Procedure T-425, which evaluation procedure is based upon a ratio of reflectances over a black background to those over a white background.

Instruments for measuring the opacity of paper as a ratio of reflectances are well known and manufactured by Bausch & Lomb and others. Unfortunately, in use of such instruments the calibration procedure required before each test reading is very time consuming, and the area of the paper sample which may be evaluated by an individual measurement is quite small and on the order of 0.625" in diameter. As a result, production personnel often do not have sufficient time to properly and thoroughly evaluate a CD (cross direction) profile test sample due to the tedious calibration procedure required and the limited size of the individual areas of the sample which may be evaluated.

Considering the tedious calibration procedure required in use of conventional paper opacity measuring instruments, and the relatively small areas of samples which may be evaluated, optical opacity evaluation by contrast ratio measurements is not a practical procedure.

OBJECTS OF THE INVENTION

An object of the present invention is to provide a method of and apparatus for measuring opacity of paper products, which may be quickly, conveniently and accurately calibrated and correlated on a day to day basis.

Another object is to provide such a method and apparatus which may be used by production personnel to obtain multiple opacity measurements of both waxed and dry opacity grades of paper on a continuous CD profile on an instantaneous basis.

A further object of the invention is to provide such a method and apparatus wherein opacity of paper is determined as a function of its light transmission characteristics.

SUMMARY OF THE INVENTION

In accordance with the present invention, there is provided a method of measuring the opacity of sheet material, such as paper, which comprises the steps of directing a beam of light onto an area of the sheet on one side thereof; sensing, on an opposite side of the sheet, the intensity of any light transmitted therethrough; and generating, in accordance with the sensed intensity of light, an indication of the opacity of the area.

In a preferred practice of the method, a voltage signal having a value in accordance with the sensed intensity of light, and thereby in accordance with the opacity of the area, is generated, and is converted to an output signal which is representative of the opacity of the area in opacity units. A visual indication of the opacity of the area in opacity units is then provided in accordance with the value of the output signal.

The invention also contemplates a system for measuring the opacity of sheet material, such as paper, which comprises a light source for directing a beam of light onto an area of the sheet on one side thereof; means for sensing the intensity of any light transmitted through the sheet; and means responsive to the sensing means for generating an indication of the opacity of the area.

In a preferred embodiment of the system, the means for sensing generates a first voltage signal having a value in accordance with the sensed intensity of transmitted light, and voltage amplifier means receives the first voltage signal and generates a second voltage signal which is an amplified representation of the first. Means are included for receiving the second voltage signal and for generating a binary representation of the value thereof, as well as for converting the binary representation to an output signal representative of the opacity of the area in opacity units. A display means then receives the output signal and provides a visible readout of the opacity of the area in opacity units.

It is contemplated that a plurality of opacity measurements may be made and averaged. Accordingly, the system also has means for averaging the values of the binary representations of the second voltage signal, and for converting the average value to a second output signal representative of the average opacities of the areas in opacity units. The display means receives the second output signal, and provides a visible readout of the average value of the opacities in opacity units. Means are included for counting the number of opacity measurements made, and second display means receives the count and provides a visible readout thereof.

The invention thus provides an improved means for rapidly, conveniently and accurately measuring the opacity of sheet material, particularly lightweight paper products. As will be described, the opacity of paper of either a waxed or nonwaxed type may be measured, and the measuring technique offers significant versatility in obtaining multiple opacity readings on a continuous basis, as compared with prior techniques which rely for opacity measurements upon a ratio of reflectances over a black background to those over a white background.

The foregoing and other objects, advantages and features of the invention will become apparent upon a consideration of the following detailed description, when taken in conjunction with the accompanying drawings.

BRIEF DESCRIPTION OF THE DRAWINGS

FIG. 1 is a cross sectional side elevation view of an apparatus for directing a beam of light against a surface of a sheet of material, and for sensing any light which passes through the sheet, and FIGS. 2A-2D together comprise a schematic representation of a circuit for receiving the sensed intensity of light passing through the sheet material and for generating a readout representative of the opacity of the material.

DETAILED DESCRIPTION

Figure 2A:
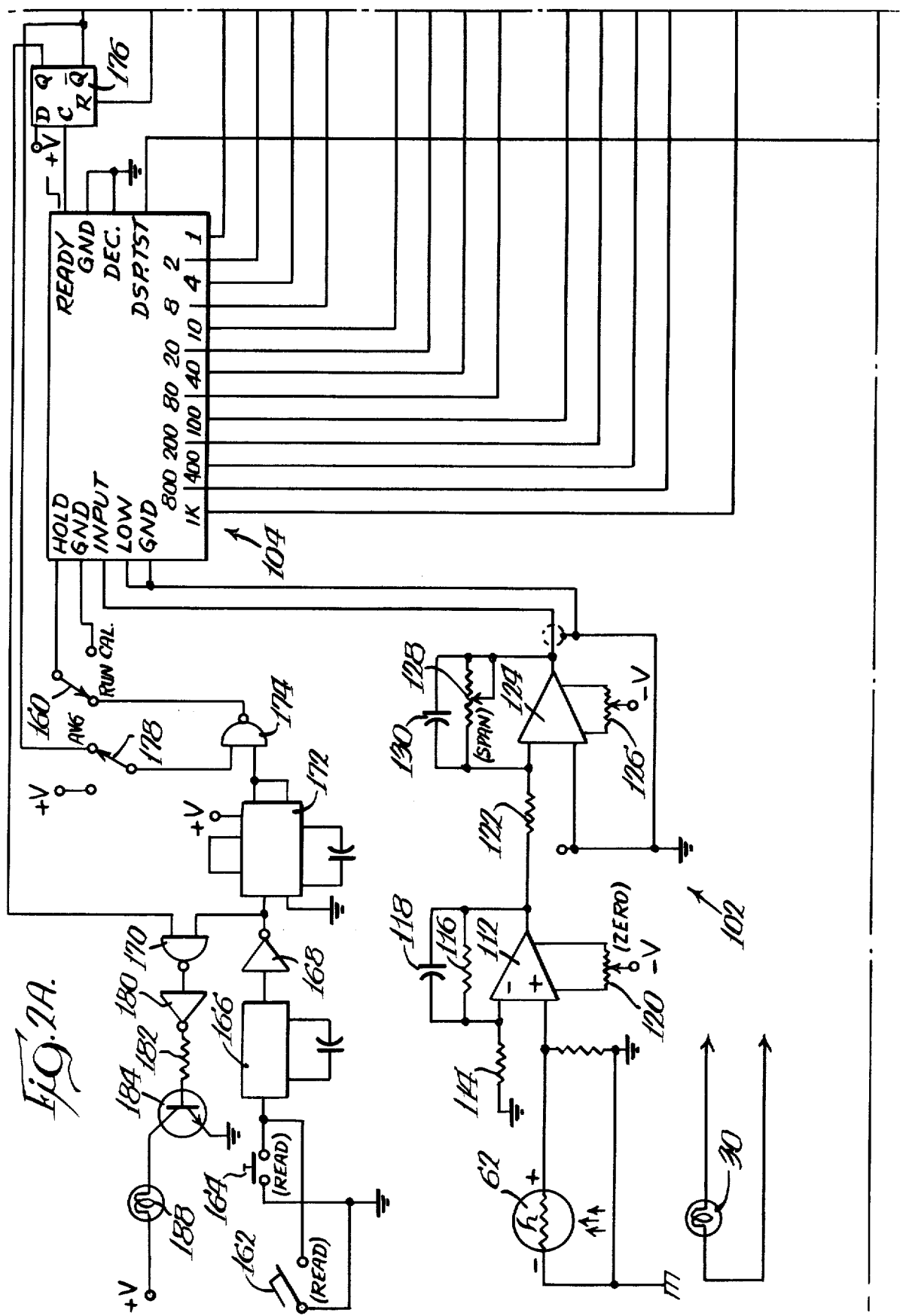

The present invention provides a method and apparatus for conveniently and accurately measuring the opacity of sheet material, and in particular the opacity of lightweight specialty packaging papers. Opacity evaluations are made by means of measuring the light transmission characteristics of the material, and the results of the measurements are displayed on a visual readout. Individual or instantaneous readouts may be obtained for each separate measurement, and after a selected number of measurements have been taken, a readout of the average opacity of the sample may be generated. The invention is equally applicable for use with both dry opaque and waxed grades of paper and provides a significantly improved means for measuring opacity as compared with conventional techniques which are based upon a ratio of reflectances over a black background to those over a white background.

Referring to FIG. 1, there is indicated generally at 10 an apparatus for directing a beam of light against a sheet of paper the opacity of which is to be measured, and for sensing the intensity of any light passing through the paper. The apparatus includes a lower frame 12 having a plurality of feet or pedestals 14 for supporting the frame on a table top, and a reinforcing member 16 for stiffening the frame. An upper frame 18 having a reinforcing member 20 is hinged to the lower frame by a pin 22, and carries a lamp housing 24 and heat shield 26. A quartz-iodide lamp 30 mounts on a lamp holder 28, and has a light emitting element within the lamp housing and heat dissipating fins 32 within the heat shield. The housing and heat shield are advantageously of aluminum and/or brass for improved heat dissipation, and a passage 34 is formed through the upper frame 18 for movement of air across the fins. A terminal block 36 connects with a pair of lamp conductors 38, whereby power may be applied to the lamp.

The lower end of the lamp housing 24 is open and connects with a cylindrical light column 40 in which is mounted a heat filter 42 and a convexo-concave lens 44. The heat filter protects the lens from the heat of the quartz-iodide lamp, and the light exiting the lens passes through a double convex lens 46 which is, together with the lens 44, in a cylindrical sleeve 48 at the bottom of the light column. The two lenses 44 and 46 form an achromatic collimating lens. A plate 50 having a 1" diameter aperture 51 is beneath the double convex lens 65 on an annular lip of the sleeve, and collimated light passes through the aperture and then through a clear glass window 52 that seals the collimator.

A sample of paper (not shown), the opacity of which is to be measured, is insertable into a space 54 between a guide plate 56 at a lower end of the sleeve 48 and a support plate 58 mounted above the lower frame 12 on a housing 60. A photronic cell 62, which by way of example may comprise a Weston Model No. 594 photronic cell, is mounted within the housing beneath the support plate. The support plate has an aperture 64 which is at least 1" in diameter and coaxially aligned with the aperture 51 through the plate 50, a diffuser lens 66 is between the photronic cell and the support plate, and an optical grade disc 68 closes the upper end of the aperture 64. The optical grade disc seals the photronic cell area from dust and dirt, the diffuser lens controls the intensity of light transmitted from the lamp 30 to the photronic cell, and a connector 70 enables an electrical connection to be made with the photronic cell, whereby the value of a signal generated thereby may be monitored.

In use of the apparatus 10, a threaded adjustment means 72 between the reinforcing members 16 and 20 is adjusted to provide an appropriate height of the space 54. Then, with a sample of paper inserted into the space, light from the lamp 30 travels through the heat filter 42, the convexo-concave lens 44 and the double convex lens 46, from whence it passes through the aperture 51 and clear glass window 52 onto the upper surface of the sample of paper. Any light which passes through the paper then travels through the optical grade disc 68 and diffuser lens 66 to the photronic cell 62. The photronic cell generates an output voltage signal having a value in accordance with the sensed average intensity of the light, which signal is processed, as will be described, to obtain an indication of the opacity of the paper. For convenient cleaning of the apparatus, its upper portion may be elevated about the hinge pin 22 to a point whereat the frame 18 rests against a stop 74.

Turning now to FIGS. 2A-2D, there is illustrated a circuit for receiving the output voltage signal from the photronic cell 62 and for generating a visual readout which may be selected to be representative of either the opacity of an individually measured 1" diameter area of a paper sample, or of the average opacity of the sample in the case where a plurality of measurements have been taken at different points. The circuit is comprised of a plurality of interconnected elements which consist, generally, of any suitable and conventional power supply 100; an amplifier means 102 for receiving and conditioning the output signal from the photronic cell; a digital panel voltmeter (DVM) 104 having a binary coded decimal (BCD) output, which records and displays the value of the output signal from the amplifier means and comprises, in the illustrated circuit, a Datel Model DM-2115B2 digital voltmeter; a microprocessor 106, which as shown comprises a Pro-Log Model PLS-898 Z80A CPU microprocessor having a 1K byte RAM and 2K byte ROM, for receiving signals from the DVM and generating converted output signals in accordance therewith; a two digit visual readout 108 which displays the number of readings or opacity measurements taken on a paper sample; and a four digit visual readout 110 which displays, in accordance with the particular microprocessor output, either the instantaneous value of an opacity measurement, or the average value of a plurality of measurements, both of which two and four digit readouts may comprise, by way of example, Dialco Model No. 739-XX60 displays.

Considering the circuit in greater detail, the amplifier means 102 includes an operational amplifier (op amp) 112 connected at its noninverting input with the output signal from the photronic cell 62 and at its inverting input with circuit common through a resistor 114. A resistor 116 and a capacitor 118 are in parallel between the output from and the inverting input to the op amp, and the offset of the op amp is adjustable by a potentiometer 120. The output from the op amp is applied through a resistor 122 to the inverting input to an op amp 124, the noninverting input to which is at circuit common. The offset of the op amp 124 may be controlled by a potentiometer 126, and the gain by a potentiometer 128 in parallel with a capacitor 130 between the output from and the inverting input to the op amp. The output voltage from the op amp 124 is applied as an input to the DVM 104, which generates on its display panel a digital reading representative of the value of the voltage. The DVM is capable of output readings from 0–1999, and a decimal point may be placed in any desired position. In practice, signals from 0–10 volts are output by the amplifier means 102 to DVM 104, and the DVM output is arbitrarily set to provide a readout from 0–100 with a one place decimal, so that one thousand discrete readings are available.

The DVM has binary weighted outputs which are applied as inputs to a plurality of tri-state buffer circuits 132, sold by Texas Instruments as Model No. 74LS367 circuits. The tri-state buffer circuits have enable inputs E, and outputs therefrom are applied to the microprocessor 106 for being received within the 1K byte RAM which temporarily receives and holds input data to be processed by the algorithm stored in the 2K byte ROM.

Some of the outputs from the microprocessor are applied to a plurality of quad latches 134, sold by Texas Instruments under Model No. 74LS175. The quad latches have reset inputs R, enable inputs E which receive other outputs from the microprocessor through inverting amplifiers 136, and outputs coupled with individual ones of the displays of the readouts 108 and 110 for energizing the readouts under control of the microprocessor. Another output from the microprocessor is applied through an inverting amplifier 138 to first inputs to each of four NAND gates 140, 142, 144 and 146, while still others of the microprocessor outputs are applied to second inputs to the NAND gates and as an enable input to a plurality of tri-state buffers 148, 150, 152, 154, 156 and 158, the outputs from which provide inputs to the microprocessor.

In use of the invention, the system is first calibrated by placing a switch 160 in a "calibrate" position. A totally opaque sample of material is then inserted into the space 54, so that no light from the lamp 28 reaches the photronic cell 62. The potentiometer 120 of the op amp 112 is then adjusted until a reading of "000.0" is displayed by the DVM 104. The totally opaque material is then removed, so that full light intensity reaches the photronic cell, and the potentiometer 128 of the op amp 124 is adjusted until the DVM display reads "100.0". This calibrates the zero and 100% values of the system, so that the DVM then applies to the microprocessor binary signals which accurately represent the intensity of light striking the photronic cell for all intensities from zero to full intensity. The switch 160 is then returned to a "run" position.

After calibration, the system is ready for use in measuring the opacity of paper samples. Thus, and with a paper sample inserted in the space 54 between the lamp 28 and the photronic cell 62, either a foot switch 162 or a hand operated switch 164 is momentarily closed to apply circuit common to a debounce circuit 166, of a type sold by Motorola under Model No. MC14490P. The debounce circuit determines the validity of the closing of the switch, and then applies an output through an inverting amplifier 168 to one input to a NAND gate 170 and to a one shot circuit 172 having a time out interval of about 10 microseconds. The output from the one shot is applied to one input to a NAND gate 174, the output from which is normally connected through the switch 160 to a "hold" input to the DVM 104. A "ready" output from DVM 104 is applied as an input to a flip-flop 176, a reset input to which receives the output from the NAND gate 146. An inverted output from the flip-flop is applied to both the inverting amplifier 158 and through a switch 178 to a second input to the NAND gate 174, and the noninverted output from the flip-flop is applied to a second input to the NAND gate 170. The output from the NAND gate 170 is coupled through an inverting amplifier 180 and a resistor 182 to the base of an npn transistor 184, which controls energization of a lamp 188.

With a switch 190 set to either a "wax" or "no wax" position, depending upon the nature of the paper sample, upon closure of one of the switches 162 and 164 the DVM 104 provides a digital readout at its panel, and applies a binary output signal through the tri-state buffer circuits 132 to the microprocessor 106. The binary output signal is representative of the value of the voltage at the input to the DVM, and therefore of the opacity of the sampled area of the paper since the intensity of light passing through the paper sample and impinging upon the photronic cell is directly related to the opacity. At the same time, control signals are coupled with the microprocessor inputs as determined by the signal at the output therefrom connected with the enable inputs to the tri-state buffers 148, 150, 152, 154, 156 and 158. This causes the microprocessor to apply to the quad latches 134, of the readout 110, converted signals which are representative of the opacity of the sampled area of the paper sample in B & L (Bosch & Lomb) opacity units, which are the standard opacity units used in the paper making industry, whereby the readout 110 displays the opacity directly in B & L opacity units. At this time the microprocessor also applies an input to the quad latches 134 associated with the readout 108 to advance by one the displayed count. The paper sample may then be moved to position a new sample area between the lamp and the photronic cell, and a new opacity measurement made.

The system requires a finite amount of time to receive and evaluate each opacity measurement, and for this purpose the lamp 188, along with its associated circuitry, have been provided. Should an operator initiate a new opacity measurement before the system has finished processing the previous measurement, the measurement will not be entered and the lamp will be illuminated to generate a visual warning, whereby an operator will be advised of the need to repeat the measurement.

As previously described, the microprocessor 106 includes a RAM, which receives and temporarily stores the data input from the DVM 104, and a ROM which holds the program for the processing algorithm. In response to each opacity measurement, the instantaneous value of the opacity in B & L units is displayed by the readout 110, and the "number of measurements" count presented by the readout 108 is advanced. The readout 108 has two numeral displays, and the system is capable of obtaining and processing up to ninety-nine individual opacity measurements, and generating at the readout 110 the average value of the measurements. Accordingly, once a desired number of individual opacity measurements have been taken at different positions on a paper sample, as indicated by the readout 108, the average value of the measurements may be obtained by momentarily closing a switch 192, which applies an input to an inverting amplifier 194 through a debounce circuit 196. The output from the inverting amplifier is applied as an input to a flip-flop circuit 198, which also receives a signal at its reset input from the NAND gate 144. This generates a signal at the inverted output from the flip-flop, which is applied through an inverting amplifier 200 and a resistor 202 to the base of an npn transistor 204 to light a lamp 206, as well as to an input to the inverting amplifier 156, the output from which is applied to the microprocessor 106 to cause it to generate at the readout 110 the average value of the opacity measurements. Closure of the switch 192 also prevents or stops any further opacity measurements from being taken until the circuit is cleared or reset.

To clear or reset the circuit in preparation for obtaining another plurality of opacity measurements, a switch 208 is momentarily closed to apply an input to an inverting amplifier 210 through a debounce circuit 212. This causes the inverting amplifier to apply an input to a flip-flop circuit 214, which is coupled at its reset input with the output from the NAND gate 142, and the inverted output from the flip-flop is applied through the inverting amplifier 152 as a reset input to the microprocessor 106.

A lamp 216 is associated with the "clear" circuit, and is illuminated when the system is first turned on or when any other actuated function is completed. The lamp is driven by a transistor 218, which connects at its base with the output from an inverting amplifier 220 through a resistor 222. The input to the inverting amplifier is obtained from an inverted output of a flip-flop circuit 224, a set input to which is coupled with the output from a NAND gate 226 and a reset input to which is coupled with the output from the NAND gate 142. The NAND gate 226 has two inputs, and one receives the output from the NAND gate 144 and the other the output from the NAND gate 140. Actuating the switch 208 clears the microprocessor of previously stored data and, if the lamp 216 is illuminated, extinguishes the lamp.

To test for proper operation of the circuit, closure of a switch 228 applies an input through a debounce circuit 230 to an inverting amplifier 232. The output from the inverting amplifier is applied as an input to a flip-flop circuit 234, a reset input to which is coupled with the output from the NAND gate 140. The inverted output from the flip-flop is applied to the microprocessor through the inverting amplifier 148, through an inverting amplifier 236 and a resistor 238 to the base of a transistor 240 to illuminate a lamp 242, and to both inputs to a NAND gate 244, the output of which connects with the base of an npn transistor 246 through a resistor 248. The emitter of the transistor is at circuit common, and the collector is connected with a test input to the DVM 104. Upon closure of the switch 228, the lamp 242 is illuminated (as well as the lamp 216), and inputs are applied to both the DVM and the microprocessor. This causes the panel display on the DVM to be illuminated, and cycles all of the display elements of the readouts 108 and 110 from 0-9, to ensure that the panel readouts are operating properly.

The invention thus provides an improved means for rapidly, conveniently and accurately measuring the opacity of sheet material, particularly lightweight paper materials. The opacity of paper of either the waxed or nonwaxed variety may be measured, and the particular measuring technique offers significant versatility in obtaining multiple opacity readings on a continuous CD profile, as compared with prior techniques which rely upon a ratio of reflectances over a black background to those over a white background.

While embodiments of the invention have been described in detail, various modifications and other embodiments thereof may be devised by one skilled in the art without departing from the spirit and scope of the invention, as defined in the appended claims.

What is claimed is:

1. A method of measuring the opacity of sheet material, such as a sheet of paper, comprising the steps of directing a beam of light onto an area of the material on one side thereof; sensing on an opposite side of the material the intensity of any light transmitted through the material; and generating an indication, in accordance with the sensed intensity of light, of the opacity of the area, wherein a plurality of measurements of the opacities of different areas of the sheet material are made, including the further steps of counting the number of opacity measurements made; averaging the values of the measured opacities and, upon occurrence of a selected count, generating an indication of the average opacity of the areas.

2. A method of measuring the opacity of sheet material, such as a sheet of paper, comprising the steps of directing a beam of light onto an area of the material on one side thereof; sensing, on an opposite side of the material, the intensity of any light transmitted through the material; generating a voltage signal having a value in accordance with the sensed intensity of light, whereby the value of the voltage signal is representative of the opacity of the area; and generating an indication, in accordance with the value of the voltage signal, of the opacity of the area, wherein the opacities of a plurality of areas of the sheet material are measured, including the further steps of generating binary representations of the values of the voltage signals; averaging the values of the binary representations; converting the average value of the binary representations to an output signal representative of the average opacity of the areas in opacity units; counting the number of opacity measurements made; and generating a visual readout, in accordance with the output signal, of the average value of the opacity of the areas in opacity units upon occurrence of a selected count.

3. A system for measuring the opacity of sheet material, such as a sheet of paper, comprising: a light source for directing a beam of light onto an area of the material on one side thereof; means for sensing the intensity of any light transmitted through the material; and means responsive to the sensing means for generating an indication of the opacity of the area, wherein the opacities of a plurality of different areas of the material are measured, said sensing means generates voltage signals having values in accordance with the sensed intensities of light, and said indication generating means includes means for receiving said voltage signals and for generating binary representations of the values thereof, said binary representations having values in accordance with the opacities of the areas; and further including means for averaging the values of said binary representations into an output signal representative of the average opacity of the areas in opacity units; counter means for counting the number of opacity measurements made, and readout means for receiving said output signal and for providing a visible readout of the average opacity of the areas in opacity units upon occurrence of a selected count.

4. A system for measuring the opacity of sheet material, such as a sheet of paper, comprising: a light source for directing a beam of light onto an area of the material on one side thereof; means for sensing the intensity of any light transmitted through the material and for generating a first voltage signal having a value in accordance with the sensed intensity; voltage amplifier means for receiving said first voltage signal and for generating a second voltage signal which is an amplified representation of said first signal; means for receiving said second voltage signal and for generating a binary representation of the value thereof; means for converting said binary representation of the value of said second voltage signal to an output signal representative of the opacity of the area in opacity units; and display means for receiving said output signal and for providing a visible readout of the opacity of the area in opacity units, wherein a plurality of opacity measurements are made and a plurality of said second voltage signals and binary representations thereof are generated, including means for averaging said plurality of binary representations; means for converting said averaged binary representations to a second output signal representative of the average opacities of the areas in opacity units; and means for counting the number of opacity measurements made, said display means providing the visible readout of the average opacities upon occurrence of a selected count.

* * * * *